United States Patent
Duckett, III

(10) Patent No.: US 11,602,267 B2
(45) Date of Patent: Mar. 14, 2023

(54) ENDOSCOPIC SYSTEM INCORPORATING MULTIPLE IMAGE SENSORS FOR INCREASED RESOLUTION

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 207 days.

(21) Appl. No.: 17/006,230

(22) Filed: Aug. 28, 2020

(65) Prior Publication Data

US 2022/0061643 A1    Mar. 3, 2022

(51) Int. Cl.

| | |
|---|---|
| *A61B 1/05* | (2006.01) |
| *A61B 1/00* | (2006.01) |
| *G02B 6/42* | (2006.01) |
| *G06T 3/60* | (2006.01) |
| *G06T 5/50* | (2006.01) |
| *G06T 7/00* | (2017.01) |

(52) U.S. Cl.
CPC ............ *A61B 1/05* (2013.01); *A61B 1/00096* (2013.01); *G02B 6/4214* (2013.01); *G06T 3/60* (2013.01); *G06T 5/50* (2013.01); *G06T 7/0012* (2013.01); *G06T 2207/10068* (2013.01)

(58) Field of Classification Search
CPC ............ A61B 1/00009; A61B 1/00045; A61B 1/000179; A61B 1/00188; A61B 1/045; A61B 1/05; A61B 1/051; A61B 1/042; G02B 6/4214; G06T 3/60; G06T 5/50
See application file for complete search history.

(56) References Cited

U.S. PATENT DOCUMENTS

| | | | |
|---|---|---|---|
| 4,940,309 | A | 7/1990 | Baum |
| 5,194,959 | A | 3/1993 | Kaneko |
| 5,689,365 | A | 11/1997 | Takahashi |
| 6,476,851 | B1 | 11/2002 | Nakamura |
| 6,659,940 | B2 | 12/2003 | Adler |
| 7,211,042 | B2 | 5/2007 | Chatenever |
| 7,372,642 | B2 | 5/2008 | Rohaly |
| 7,746,568 | B2 | 6/2010 | Rohaly |
| 8,360,964 | B2 | 1/2013 | Ertas |

(Continued)

FOREIGN PATENT DOCUMENTS

| | | |
|---|---|---|
| EP | 1429540 A1 | 6/2004 |
| JP | S6088924 | 5/1985 |
| WO | WO199418789 | 8/1994 |

*Primary Examiner* — Aaron B Fairchild
*Assistant Examiner* — Julianna J Nicolaus
(74) *Attorney, Agent, or Firm* — David Noel Villalpando

(57) ABSTRACT

An endoscope or other endoscopic instrument is provided with multiple image sensors, each capturing a portion of the image provided from an optical imaging system. One sensor receives two portions of the image light at opposing sides of the image. The output from the multiple sensors is combined and manipulated into a single high resolution image which can then be displayed to the user. A virtual horizon rotation feature is also provided which can rotate a displayed image within a combined field of view including data from the multiple image sensors. Various light directing element designs are provided to direct image light to the multiple sensors.

28 Claims, 14 Drawing Sheets

(56) References Cited

U.S. PATENT DOCUMENTS

| | | | |
|---|---|---|---|
| 8,928,746 B1 | 1/2015 | Stevrin | |
| 9,557,634 B2 | 1/2017 | Cheng | |
| 2001/0022858 A1 | 9/2001 | Komiya | |
| 2002/0057341 A1* | 5/2002 | Tanaka | H04N 7/181 |
| | | | 348/E7.086 |
| 2004/0001145 A1 | 1/2004 | Abbate | |
| 2007/0188650 A1* | 8/2007 | Kobayashi | H04N 5/2258 |
| | | | 396/323 |
| 2011/0292258 A1* | 12/2011 | Adler | G02B 23/2423 |
| | | | 348/263 |
| 2012/0053407 A1 | 3/2012 | Levy | |
| 2012/0057000 A1* | 3/2012 | Rohaly | G02B 27/106 |
| | | | 348/E13.074 |
| 2012/0320165 A1 | 12/2012 | Schuck | |
| 2013/0041226 A1 | 2/2013 | McDowell | |
| 2014/0098429 A1 | 4/2014 | Morita | |
| 2014/0364694 A1* | 12/2014 | Avron | A61B 1/00181 |
| | | | 600/164 |
| 2014/0375784 A1 | 12/2014 | Massetti | |
| 2015/0062299 A1 | 3/2015 | Brown | |
| 2015/0238071 A1* | 8/2015 | Hua | A61B 1/3132 |
| | | | 600/109 |
| 2016/0037082 A1 | 2/2016 | Wang | |
| 2016/0057405 A1 | 2/2016 | Duckett | |
| 2017/0155818 A1 | 6/2017 | Bonnet | |
| 2018/0196251 A1* | 7/2018 | Duckett, III | A61B 1/00188 |

* cited by examiner

ENDOSCOPIC SYSTEM INCORPORATING MULTIPLE IMAGE SENSORS FOR INCREASED RESOLUTION

BACKGROUND OF THE INVENTION

Field of the Invention

This invention relates to high resolution video endoscopes, and in particular to a scope using multiple sensors to provide high resolution images.

Description of the Background Art

The invention relates to optical instruments such as endoscopes, exoscopes, and borescopes having an image sensor assembly at the distal end of the instrument shaft or, more preferably, with an image sensor assembly as part of a camera head connected to an endoscope. In some particular embodiments, the invention relates to image sensing systems that can produce a combined image from multiple image sensors located within the distal end of the instrument shaft, and to optical instruments incorporating such image sensing systems.

Instruments such as endoscopes and borescopes are used to allow a visual inspection of locations which are not readily accessible. For example, endoscopes are typically (although not exclusively) used in medical applications to provide a view of an area within a patient's body. Whether employed for medical or other applications, the instrument typically includes an elongated shaft of relatively small diameter extending from a handle to a distal end.

An imaging or viewing arrangement is included with the instrument to allow a user to obtain a view from the shaft distal end. This arrangement may include a system of lenses and a light conduit through the shaft to direct an image from the distal end to an eyepiece associated with the instrument handle. Alternatively, the imaging or viewing arrangement may include an electronic imaging device at the distal end of the instrument shaft. Such an electronic imaging device collects image data and communicates that data through the shaft and handle ultimately to a processing system that assembles the data to produce an image displayed on a suitable display device.

Depending upon the procedure for which the instrument is used, it may be necessary for the operator to view a relatively large area or view a relatively small area from different angles. In a medical procedure for example, the operator may desire to view a location which is larger than the field of view of the imaging collecting arrangement of the endoscope or view a location from different angles. It is therefore desirable to have an endoscope with a wide-angle viewing area, or with the capability to change the viewing angle. It is also desirable to provide the highest resolution possible for image display, and, particularly, for image capture, enabling thereby the ability to digitally zoom in on an region of interest (ROI), and digitally pan through the collected image, while still viewing the image at a resolution preferably at least equivalent to that of the display monitor. However, power and space limitations must be taken into consideration when utilizing high resolution image sensors.

A flexible endoscope that allows panning the image without moving the scope tip is found in U.S. Pat. No. 8,771,177B2 to Hale et al., which is commonly owned with the present invention. This scope uses a wide angle lens positioned at an angle to the center axis of the scope to focus light from the front and sides of the scope. The light is focused on a high resolution sensor, along which a desired area is selected to produce an image that can be digitally panned along the range of view covered by the wide angle lens. The scope shaft is flexible, and the high-resolution sensor is positioned in a distal end portion of the shaft.

U.S. Pat. No. 8,360,964 to Ertas describes a wide-angle, high definition endoscope that includes at least two optical imaging channels. Two lenses are present at the scope distal tip, having different fields of view in complementary directions. Received images are transmitted along separate optical channels along the longitudinal axis of the endoscope to a single camera head that contains a wide screen image sensing device. The images directed along the independent optical channels fall onto a common sensor, each of the respective images overlapping, resulting in a wider angle image being detected by the image sensor.

U.S. Pat. No. 9,986,899 discloses an endoscopic instrument including multiple objective lens systems, and corresponding multiple optical channels, each distinct optical channel directing collected image light from its corresponding field of view onto one or more image sensors. Image processing subsequently generates a single, simulated wide angle image from the multiple images collected.

U.S. Publication No. 2015/0062299 describes a relatively large endoscope including two electronic-cameras arranged side-by-side facing along scope axis to create stereo picture pairs to permit quantitative three-dimensional (3D) imaging and analysis.

U.S. Pat. No. 8,675,291 discloses a system to provide a three-dimensional image using a single objective lens to collect light from an image space. The collected image beam is then passed through a stop containing a plurality of apertures, each aperture collecting light of the image scene from a different perspective. Each corresponding sub-beam is directed along its corresponding one of multiple optical channels, to a corresponding image sensor, and the multiple collected images, each with an individual perspective of the image scene, are used to provide a three-dimensional image of the scene.

U.S. Pat. Nos. 7,783,133 and 7,211,042, and U.S. Publication No. 2014/0375784 describe various techniques to counter-rotate an image produced from an endoscope image sensor and thereby achieve a constant, user-defined horizon.

U.S. Pat. No. 10,571,679, filed Jan. 6, 2017, and issued Feb. 25, 2020, by the inventor of the present application, as well as co-pending continuation U.S. application Ser. No. 15/733,999, filed Jan. 3, 2020, both citations hereby incorporated by reference, disclose a single optical channel system, wherein a wide angle lens is employed to capture a wide field of view, and the incoming image is split, in image space, onto two or more image sensors, the resulting image data is then stitched together by an image processing system, to create a single wide angle image of higher resolution that would be possible with only a single image sensor of the size employed by the inventive systems.

As mentioned previously image sensors with adequately high resolution can often be too large to fit into the distal tip of an endoscope, limiting thereby image resolution for distal tip sensor endoscopes. One example of a sensor of adequate quality, available at the time of filing, that is capable of fitting into the distal end of a 10 mm diameter endoscope is an HD (1080p) sensor. With current technology, it is difficult with a shaft size smaller than 10 mm to house an image sensor of HD resolution or higher. Corresponding problems are associated with the use of state-of-the-art, high resolution image sensors, such as the "8k Ultra HD" image sensors currently available, having a display resolution width of approximately 8000 pixels. Such sensors are generally too large to fit into conventional endoscopic camera heads and are the source of other practical problems associated with their high power consumption and heat generation.

There remains a need for ways to provide higher resolution capabilities for endoscopes both in circumstances when a small bore diameter is desired and also wherein high resolution images are to be proximally captured. There also remains a need in the art to provide an optical instrument such as an endoscope that allows the collection of wide-angle perspectives of the image scene as well as high resolution image capture, while remaining within the practical limitations required by endoscopy. In addition, there is a need for endoscopes which require a minimum amount of video processing to the collected images and that provide the highest quality image in the regions of interest.

SUMMARY OF THE INVENTION

An endoscope or other endoscopic instrument is provided with multiple image sensors, each capturing a portion of the image provided from an optical imaging system. One sensor receives two portions of the image light at opposing sides of the image. The output from the multiple sensors is combined and manipulated into a single high resolution image which can then be displayed to the user. A virtual horizon rotation feature is also provided which can rotate a displayed image within a combined field of view including data from the multiple image sensors. Various light directing element designs are provided to direct image light to the multiple sensors.

According to a first aspect of the invention, an optical instrument system includes an endoscopic instrument. The endoscopic instrument includes an optical channel assembly, first and second image sensors, and first and second light directing elements. The optical channel assembly includes a single channel lens system optically arranged to receive image light from an object space and condition the image light in a single optical channel to create an image space. The first image sensor is positioned to receive a first portion, but not all, of the image light, the first portion corresponding to a first central area of an optical image, and the second sensor is positioned to receive a second portion and a third portion of the image light from opposing sides of the image with respect to the first portion and at least substantially different from the first portion. The first and second light directing elements are positioned in the image space of the optical channel assembly to receive the second and third portions of the image light from the optical channel assembly and direct them toward respective first and second portions of the second image sensor.

According to a second aspect of the invention, a method provides images through an endoscope. The method includes receiving image light at a distal lens of an optical channel assembly and passing the image light through a single optical channel path toward an image space. A first portion of the image light is received from the optical channel assembly with a first image sensor, the first portion of the image light forming a first image of a first part of the field of view of the distal lens. Second and third portions of the image light are received from the optical channel assembly with a second image sensor, the second and third portions of the image light from opposing sides of the image light with respect to the first portion and forming a second and third images of second and third parts of the field of view of the distal lens at least substantially different from the first part of the field of view. The method includes combining, with an image processor, the first, second, and third images to produce a displayed image.

According to a third aspect of the invention, a method provides images through an endoscope. The method includes receiving image light at a distal lens of an optical assembly and passing the image light through a single optical channel path toward an image space. A first portion of the image light is received from the optical channel assembly with a first image sensor, with a first sensor height smaller than a first sensor width, the first portion of the image light forming a first image of a first part of the field of view of the distal lens. Second and third portions of the image light are received from the optical channel assembly with a second image sensor, the second and third portions of the image light from opposing sides of the image light with respect to the first portion and forming a second and third images of second and third parts of the field of view of the distal lens at least substantially different from the first part of the field of view. An available image data area is provided as the image data collected by the first portion of the second sensor, the first sensor, and the second portion of the second sensor. A digital zoom signal indicator is received indicating a portion of the available image area as a desired image area to be displayed. If the desired image area spans only image data contained in the first image, the method produces a displayed image from the image data collected from only the first sensor. if the desired image area spans image data from the first and the second or third images, the method includes combining, with an image processor, data from the first image and one or both of the second and third images to produce a displayed image.

According to some implementations of above aspects, the optical channel assembly extends from a distal end portion of an instrument shaft coupled to a proximal camera head holding the first and second image sensors. The optical channel assembly may be housed in a distal end portion of an instrument shaft with the first and second image sensors.

According to some implementations of above aspects, the first portion of light partially overlaps with at least one of the second and third portions of light.

According to some implementations of above aspects, an optical system includes a processing unit operatively coupled to the first and second image sensors to receive first and second image data from the sensors and operable to combine image data from the first and second image data into a displayed image including image data from the first and second portions of the second image sensor positioned at opposite sides of the displayed image with the first image data displayed there between. The processing unit may be further operable to receive a zoom input control, and in response alter the displayed image to display an enlarged portion of the displayed image including only image data received from the first image sensor. The processing unit may be further operable to, when a user rotates the endoscopic instrument around an instrument shaft, rotate a displayed image to provide a view with a constant horizon. The processing unit may be further operable to detect when a zoomed image is produced entirely within the area of the image data received from the first image sensor, and further operable to disable image processing necessary to combine the first and second image data. The processing unit may be further operable to: detect, when a user rotates the endoscopic instrument around an instrument shaft, if a zoomed image is produced with a diagonal of zoomed image entirely within the area of image data received from the first image sensor, and electronically rotate a displayed image to provide a view with a constant horizon, and disable image processing necessary to combine the first and second image data.

According to some implementations of above aspects, the second and third portions of the image light are directed toward the second image sensor along an optical axis that is non-parallel to the longitudinal axis. The plane of the second image sensor may be at an angle slightly offset from parallel to the longitudinal axis.

According to some implementations of above aspects, the first light directing element includes a prism which passes the first portion of light to the first sensor and redirects the second portion of the image light to the second sensor. The second light directing element may include a mirror or a reflective prism.

According to some implementations of above aspects, a third light directing element redirects the first portion of image light toward the first sensor. The third light directing element may include reflective surfaces positioned to direct the second and third portions of light.

According to some implementations of above aspects, the second portion of image light and the third portion of image light are reflected with at least two reflective elements to provide a similar image orientation to the first portion of image light.

According to some implementations of above aspects, responsive to a user rotating the endoscopic around an instrument shaft, a displayed image is rotated to provide a view with a constant horizon, the displayed view being comprised entirely of image data collected from the first sensor if the desired image area spans only image data contained in the first image, and the displayed view including combined data from the first and one or both of the second and third images if the desired image area spans image data from the first and the second or third images.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 2A is a cross section block diagram of a proximal detection implementation of the present invention, while

DETAILED DESCRIPTION OF THE DRAWINGS

As used herein, elements (e.g., sensors and lenses) that are "optically arranged" in relation to other elements, refers to the element's position along an optical path shared by first and other elements. For example, a relay lens group optically arranged between an image sensor and an objective, means that the relay lens group occupies a portion of the optical path that light travels (i.e., from the objective to the image sensor) for capturing images or video. "Optical image" is an image formed by the light rays from a self-luminous or an illuminated object that traverse an optical system or element.

Figure 1:
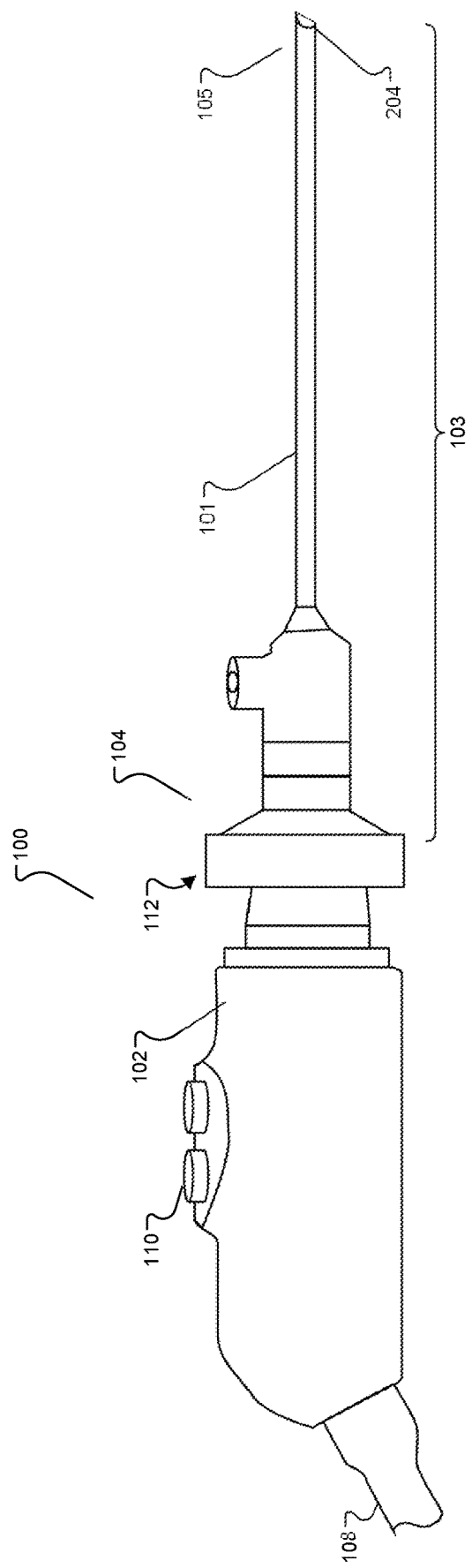
FIG. 1 is a perspective view of an endoscope instrument according to an example embodiment.

Referring to FIG. 1, depicted is a perspective view of an instrument 100 employing multiple proximal image sensors according to one aspect of the present invention and generally includes a scope element 103 including an elongated shaft 101, the scope element being connected to a camera head 102. The scope 103 can be detachably connected to the camera head 102 by any means known in the art, such as a bayonet connector 112, the elements may be parts of a single instrument 100. Shaft 101 extends from a proximal end shown generally at reference numeral 104 connected to camera head 102 to a distal end generally indicated at reference numeral 105. A distal end portion is included at the shaft distal end 105. An objective lens 204, often a wide angle lens, is located at the distal end portion, although it is not shown in FIG. 1 due to the scale of the figure. The rigid, elongated shaft 101 generally comprises a relay lens system, such as a series of coupled rod lenses, to transmit an image collected by the objective lens 204 to the proximal 104 portion of the scope 103. The image is then received by the camera head 102. The shown shaft 101 is a rigid implementation, but flexible-shaft implementations are also possible, as well as implementations wherein the image sensors and associated optics are placed in the distal end of the scope 105.

Camera head 102 receives electrical operating power through a cable 108 which extends from a proximal end of camera head 102 in this example instrument. This power may be used to operate one or more light sources or, in some embodiments, such as those with distally placed image sensors, other electronic elements mounted within distal portion 105, including multiple electronic image sensors. Data signals from such an imaging device, where image sensors are distally placed, may be communicated through appropriate conduits within shaft 101 and handle 102 to cable 108. These data signals may be communicated through cable 108 to processing equipment (not shown) which processes the image data and drives one or more video monitors to display the images collected by the instrument 100. Those familiar with endoscopes and borescopes will appreciate that instrument 100 includes a number of additional features such as controls 110 for controlling the operation of the instrument. Although data transmission relating to the image sensors will be described further below, the general operation and control of instrument 100 will not be described further herein in order to avoid obscuring the present invention in unnecessary detail. Preferably the designs and techniques herein are employed as improvements to a endoscopic system with image sensors proximally present in the camera head 102, but are also relevant to a distal mounted image sensor arrangement, such as, for example, the endoscopic system described in U.S. Pat. No. 8,814,782 to Hale, et al., issued Aug. 26, 2014, which is incorporated by reference.

Figure 2A:
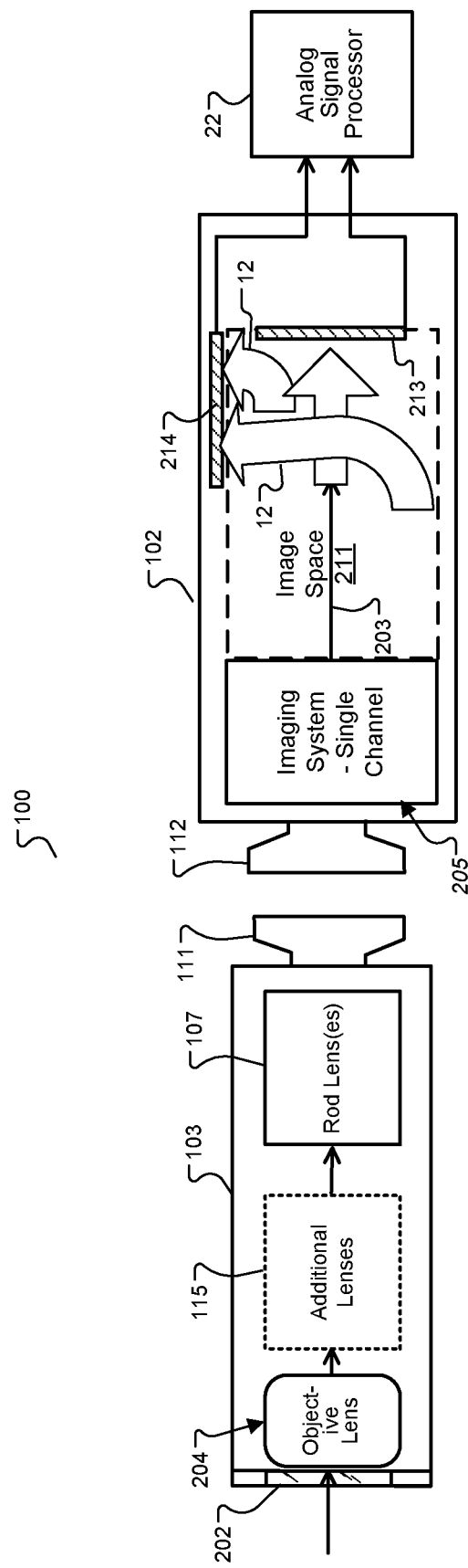

FIG. 2 shows block diagrams for two different implementations of the present invention. In order to improve clarity, elements common to both example implementations shown in FIG. 2 are not explicitly discussed in both implementations, where they may perform different functions. FIG. 2A shows a cross section diagram of a scope 103 separably connected with the eyecup 111 attaching with a bayonet connector 112 to a camera head 102. Light from an object scene passes through a cover glass 202, and objective lens 204 as well as any other additional lenses 115 necessary to shape or condition the light before passing on to a relay lens system 107, generally including a series of rod lens pairs. Image light then passes into a camera head 102 and is received by a single channel imaging system 205 that focuses the light to fall onto image sensors 213, 214. Located within the image space 211 of the single optical channel are light directing elements 12 directing some, but not all, of the incoming image light in toward one image sensor 214, while the remaining image light falls upon another image sensor 213. Analog signal processor 22 processes the collected image information, as will be further discussed below.

Figure 2B:
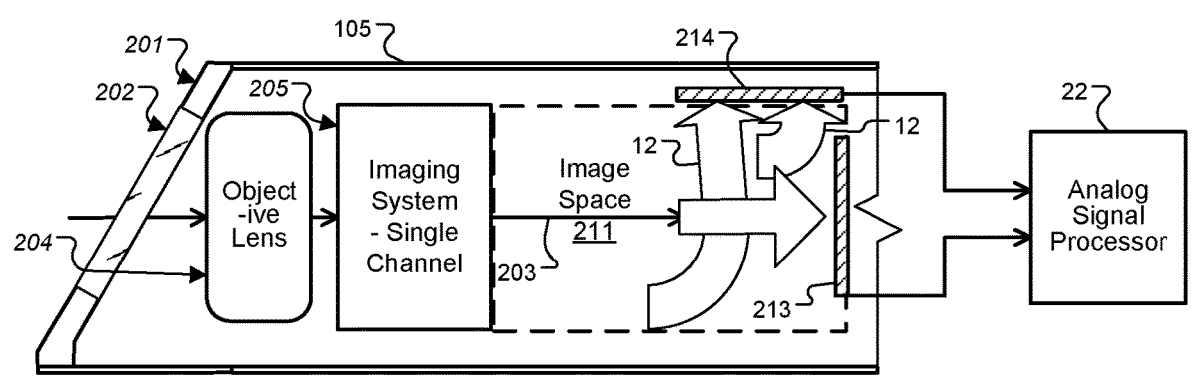
FIG. 2B is a cross section block diagram of a distal end of an instrument shaft according to an example embodiment of the invention.

FIG. 2B, represents a cross section block diagram of an alternate distal tip implementation of the present invention. Depicted is the distal end portion 105 of shaft 101 having a cover glass 202 in an inset position at its distal face 201. Optically arranged at the interior side of cover glass 202 is an optical channel assembly positioned in the distal end portion 105, including an objective lens with negative optical power 204 having distal and proximal sides positioned to receive image light from an object space (the area to be imaged) at the distal side of lens 204 and pass the image light to the proximal side. In distal sensor embodiments, the distal end portion will be connected, either through a rigid or flexible extended shaft to a handle element, somewhat analogous to the camera head element 102 of proximal sensor embodiments, wherein any desired operation controls may be located.

In wide-angle implementations, the field of view of the optical channel assembly may be between 60 and 180 degrees. Wide-angle implementations may include a fisheye lens as an optical element of a wide-angle lens system. The wide-angle lens system may be partially- or fully-defined by the optical channel assembly.

In the embodiment shown in FIG. 2B, cover glass 202 and lens 204 are fixed at a 30 degree angle from the scope axis, however in other versions, such as that shown in FIG. 2A, a non-angled face may be used, or some other angle such as 45 degrees may be used. The optical channel assembly typically includes lens 204 and a single channel imaging system 205 of one or more prisms, lenses, lens groups, or other optical elements optically arranged at the proximal side of lens 204 to receive the image light as a beam and focus, disperse, or otherwise modify the beam. By "single channel", it is meant that a beam of light forming a single image is passed through a common lens group or set of optical elements with a single perspective.

An optical channel assembly 205 generally directs the light toward an image space 211 of the optical channel assembly 205. While the space is depicted as a gap in the drawings, a smaller gap or no gap may be present in some implementations, with the image, as discussed below, split within the image space of the system. At least two image sensors 213 and 214 are positioned in the distal end portion 105 to receive light from the image space.

In both distal and proximal detection systems, the first image sensor 213 is positioned to receive a first portion, but not all, of the image light corresponding to a first area, in most embodiments, a central area, of an image observed by the endoscope, and the second sensor 214 is positioned to receive a second and third portions of the image light redirected in the image space 211 by the light directing elements 12 and corresponding to second and third areas of the observed image. The second and third portions of the image light are from opposing sides of the image light with respect to the first portion and at least substantially different from the first portion. In this embodiment, light directing elements 12 are positioned to direct light from separate areas, for example, above and below the central area of image space 211 toward image sensor 214.

The light directing elements 12 may be any suitable element for redirecting light, such as a prisms, mirrors, light splitters beam splitters, or fiber optic elements. Prisms are preferred because of their small size, mechanical durability and resistance to deformity.

As can be seen in these example versions, the first image sensor 213 is positioned with a sensor array pointing to receive light propagating along a local optical axis parallel to the longitudinal axis 203 of the optical channel assembly. In this figure, the sensor array is oriented substantially parallel to a longitudinal axis 203 of the instrument shaft. Second image sensor 214 is positioned with the sensor array pointing to receive light propagating perpendicularly or substantially perpendicularly to longitudinal axis 203. By substantially perpendicular, it is meant that the light propagates generally radially outward from longitudinal axis 203 such that second image sensor 214 can be arranged longitudinally as shown. The angle of image light propagation and the direction of the sensor may be offset from perpendicular to mitigate reflections, for example.

The depicted arrangement, along with other embodiments herein disclosed, allows for sensors of a greater total active array area (e.g., a light sensing area) than would ordinarily be possible to be fit into the endoscope shaft. Although in FIGS. 2, 4, 5, 6, and 7, image sensors 213 and 214 are oriented generally parallel and perpendicular to the longitudinal axis of the endoscope 203, other image sensor pointing angles may be used. For example, one or both the sensor arrays may be pointed for receiving light redirected at 45 degrees from the longitudinal axis of the endoscope, at 30 degrees, or at 60 degrees.

Image sensors 213 and 214 typically are part of at least one sensing module or assembly that includes a printed circuit board ("PCB") on which is mounted an imaging device including an image sensor with sensing array, typically having a transparent cover. The PCB or other electrical circuitry that reads the sensed signal off the image sensing array of the sensors may be of any suitable type, preferably the smallest and lowest profile available to fit in the limited space, particularly in distal tip implementations. For implementations where the image sensors are located in a camera head element, space, power and size may be considerations for selecting appropriate image sensors. The various portions of the sensor assembly are known and are not shown separately. It will be appreciated by those familiar with imaging sensors that these devices may be accompanied by electronic components such as transistors, capacitors, resistors, and regulators for example.

Additionally, imaging sensors 213 and 214 and their accompanying electronic components require electrical power and means for communicating image data to be processed for producing the collected images. The required operating power and data transmission may be provided through a suitable electrical cable or bus connection. These accompanying electronic components and the power/data cable are omitted from the present drawings in order to more clearly illustrate the various features of the imaging apparatus.

Those skilled in the art will appreciate that the electronic components and power/data cable may be connected to or included with the image sensor modules in any number of fashions. For example, some embodiments may include the electronic components mounted on the opposite side of PCB on which imaging sensor itself is mounted. The power/data cable may also be connected to the back side of PCB to provide operating power to the image sensors and allow image data to be communicated from the image sensor assembly to processing equipment remote from the shaft distal end portion 105. However, the present invention is not limited to any particular mounting arrangement for electronic components which may accompany imaging sensor and a power/data connection, although some embodiments, such as those shown in FIG. 6 and FIG. 7, may benefit from particular mounting configurations. Any accompanying electronic components and the power/data cable need only be mounted to provide the required function.

Further, although sensors 213 and 214 are shown as discreet entities, two or more of said sensors may be share, for example, a mounting substrate or housing accommodating said two or more sensors.

In FIG. 2, the image sensors 213 and 214 are connected through a power and data connection to an analog signal processor 22, which receives the analog sensor data and conditions it for processing by the digital portions of the system, as will be further described below. An analog signal processor 22 may be located in a handle for distal image sensor embodiments or the camera head 102 (FIG. 1) of the scope device or may be located elsewhere. It is understood that metal oxide semiconductor sensors (CMOS) may have incorporated with the sensor assembly some of the digitization functions, however an analog signal processor 22 may provide further signal processing and control before the image data is suitable for digital processing.

Figure 3:
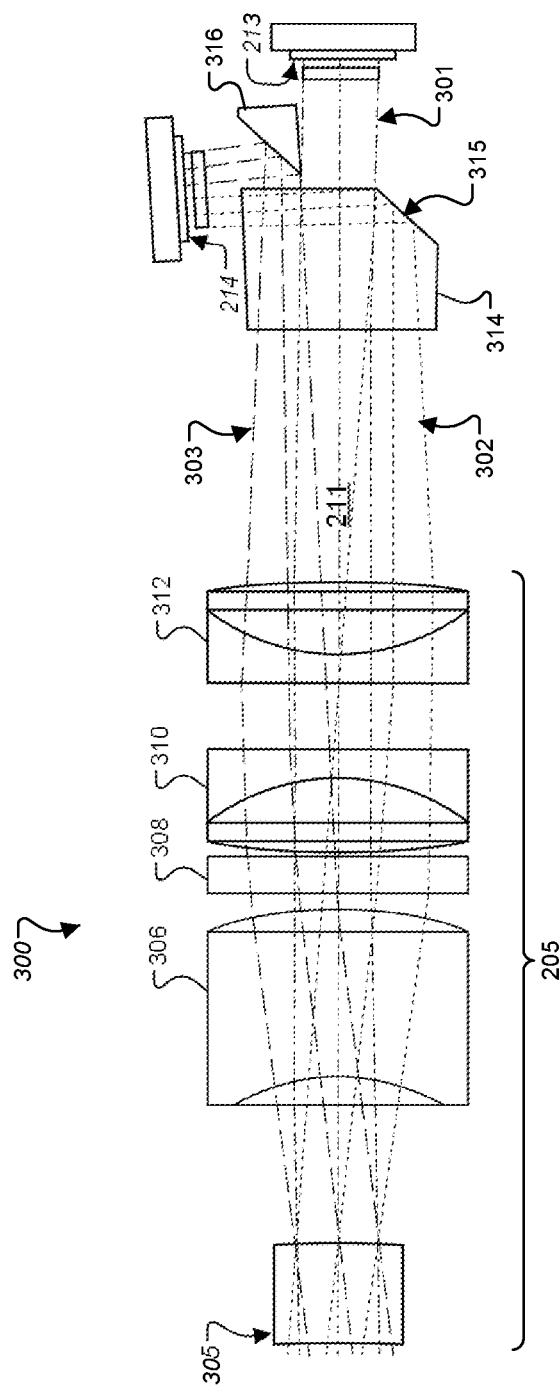
FIG. 3 shows a light ray bundle diagram for a system like that of FIG. 2.

FIG. 3 shows a light ray bundle diagram for a system such as that shown in FIG. 2, including an example optical design of an optical assembly 300 of a camera head portion of the scope according to one embodiment. The effect of optical assembly 300 can be seen in the depicted light ray bundles 301, 302, and 303 which show image light directed along the optical axis of optical assembly 300 and directed toward first image sensor 213 and second image sensor 214.

At the left is shown element 305, an element of the single channel imaging system 205, in this case a conditioning lens receiving light from the scope element into the camera head. Optically arranged or attached at the proximal side of lens 305 is a lens 306, shown here as a meniscus lens, but many different designs are possible, to spread the incoming light to an appropriate size for the imaging process downstream in the proximal direction. Next the light passes through an optional flat plate element 308, in this particular embodiment, an IR cut filter, and is received at a doublet lens 310, or other suitable lens with a slight positive power. Optically arranged to receive the image light from lens 310 is another doublet lens 312 having a slight positive power to align the image light as desired in image space 211. This particular optical channel assembly is only one of many suitable optical assemblies that may be used to prepare the incoming light for reception by the image sensors. Other appropriate optical assembly designs may be selected as required by the specific camera and/or endoscope system.

At the image space 211, the light emerges from the single channel optical system in converging rays to focus on image sensors 213 and 214. In this embodiment, a first portion of image light 301 passes straight toward first image sensor 213 through prism 314. A second portion of the image light 302 is directed to second image sensor 214 by angle prism 315, which in this embodiment is formed by a lower proximal edge of prism 314 providing a reflective surface from which the second portion of image light 302 reflects. A third portion of the image light 303 at the opposite side of first portion 301 from second portion 302 is also reflected toward second image sensor 214 by reflecting element 316. Reflecting element 316 may be a mirror or reflecting prism. In this example the angle prism 315 and reflecting element 316 are examples of light directing elements 12 (FIG. 2).

The depicted arrangement receives the first portion of the image light 301 from the optical channel assembly with the first image sensor 213, forming a first image of a first part of the field of view of the (single) optical channel assembly, and receives second and third portions of the image light 302 and 303 from the optical channel assembly with the second image sensor 214, forming second and third images of respective portions of the field of view.

As can be understood, the different portions of light make up different areas from the common image light fed to image space 211 and provide different areas of the image viewable through the scope. The image light may be maintained in the same focal conditions through light directing elements 12, which may be prisms (see, for example, FIG. 4) 408, 410, 412 or elements of a single prism (see, for example, FIG. 3) 314, or a combination of one or more prisms and/or mirrors.

As can be observed in FIG. 3, second image sensor 214 has its image sensing surface pointed at slight angle from perpendicular to the longitudinal axis of optical assembly 300 along which image light passes before being redirected. This helps to mitigate deleterious reflections and diffusion off of prism 314.

Figure 4:
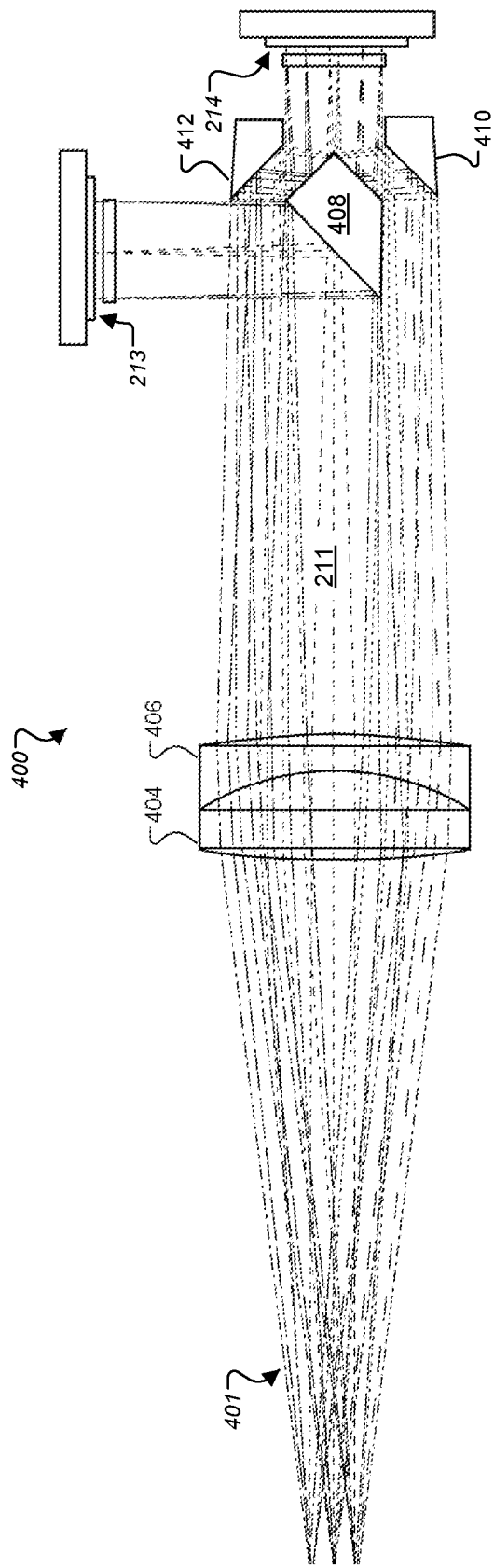
FIG. 4 shows a light ray bundle diagram for an alternative optical arrangement from that of FIG. 3.

FIG. 4 is a light ray bundle diagram of a scope optical channel assembly 400 having a different construction of light directing elements according to another embodiment. In this version, a different arrangement of two image sensors, 213 and 214, is shown with first image sensor 213 positioned facing perpendicularly to the longitudinal axis of optical assembly 400, and sensor 214 positioned in line with the longitudinal axis, but receiving image light passed through light directing elements rather than directly.

Optical channel assembly 400 may include an initial wide angle objective lens (not shown) through which light rays 401 of the image light enter the optical channel assembly, either distally placed or located in the camera head element. A convex lens 404 is optically arranged to receive the image light and pass it toward lens 406. Lens 406 is a concave-convex lens and operates to align the light rays in image space 211.

A right angle irregular prism 408 is positioned in image space 211 of optical channel assembly 400 to receive a first portion of the image light from lens 406 and direct it toward first image sensor 213. In this embodiment, prism 408 is a reflective prism having a distal surface from which the first portion of light reflects toward first image sensor 213 as depicted. In other embodiments, prism 408 may be replaced with some other light directing element, such as a mirror. Prism 408 includes an irregular proximal side with two reflecting surfaces formed to reflect second and third portions of the image light toward second image sensor 214. Two reflecting elements 410 and 412 are optically arranged in image space 211 to redirect second and third portions of the image light toward the proximal reflecting surfaces of prism 408 as depicted. Reflecting elements 410 and 412 may be reflecting prisms, mirrors, or other suitable light directing elements. The two portions of image light reflected from reflecting elements 410 and 412 pass to the proximal reflecting surfaces of prism 408 and are reflected toward second image sensor 214.

As can be understood from the ray diagram, first image sensor 213 receives a first portion image light corresponding to a first central area of an optical image, and second image sensor 214 receives second and third portions of the image light from opposing sides of the image light with respect to the first portion and at least substantially different from the first portion.

One important distinction between the operation of the embodiment of FIG. 3 and that of FIG. 4, relates to the method of recombination of the collected images and the type of image sensors used. As is known in the art, CCD image sensor generally operate in a "global shutter" mode, that is, the entire image is captured at a single instant as a single frame. By contrast, CMOS sensors frequently utilize a "rolling shutter" mode to capture the image. That is, each pixel along a row of pixels is captured sequentially, followed by the next row. Therefore, conventional rolling shutter CMOS sensors, which at the time of filing are the industry standard for small CMOS sensors, can present particular problems associated with dividing an image, in image space, and directing the resulting partial images onto different image sensors, as in the present invention. For example, in the embodiment of FIG. 3 there can be a disconnect in the acquisition time of a given line of pixels collected by the second image sensor 214 in relation to the image collected by the first sensor 213. In order to simplify the description, the "top" of the second image sensor 214 will be considered to be to the right in the Figure, and the "bottom" of the image sensor is to the left in the Figure, (corresponding to the top and bottom of the image in image space). The "top" and "bottom" of the first image sensor 213 can be considered conventionally (e.g. the arrow points to the top of the sensor). In this case, the top of the image in image space is collected in the middle of the second image sensor, and proceeds to the top of the sensor. The central part of the image is collected on image sensor 213, with the top of the central image at the top of the first sensor 213 and proceeding to the bottom of the first sensor. The bottommost portion of the image is collected, starting from the middle of the second detector 214 and proceeding to the bottommost portion of the second image sensor. This creates problems, when an embodiment like that of FIG. 3 is used with a rolling shutter image sensor, as the synchronization of the image regions will be imperfect as the collection sweeps across, in particular, the second image sensor. Other embodiments, such as that presented in FIG. 4 do not suffer from the same problems, as the double-reflection between prisms 412 and 408 result in the image captured at the second image sensor 214 being sequentially captured top to bottom, rather than from the center out.

Figure 5:
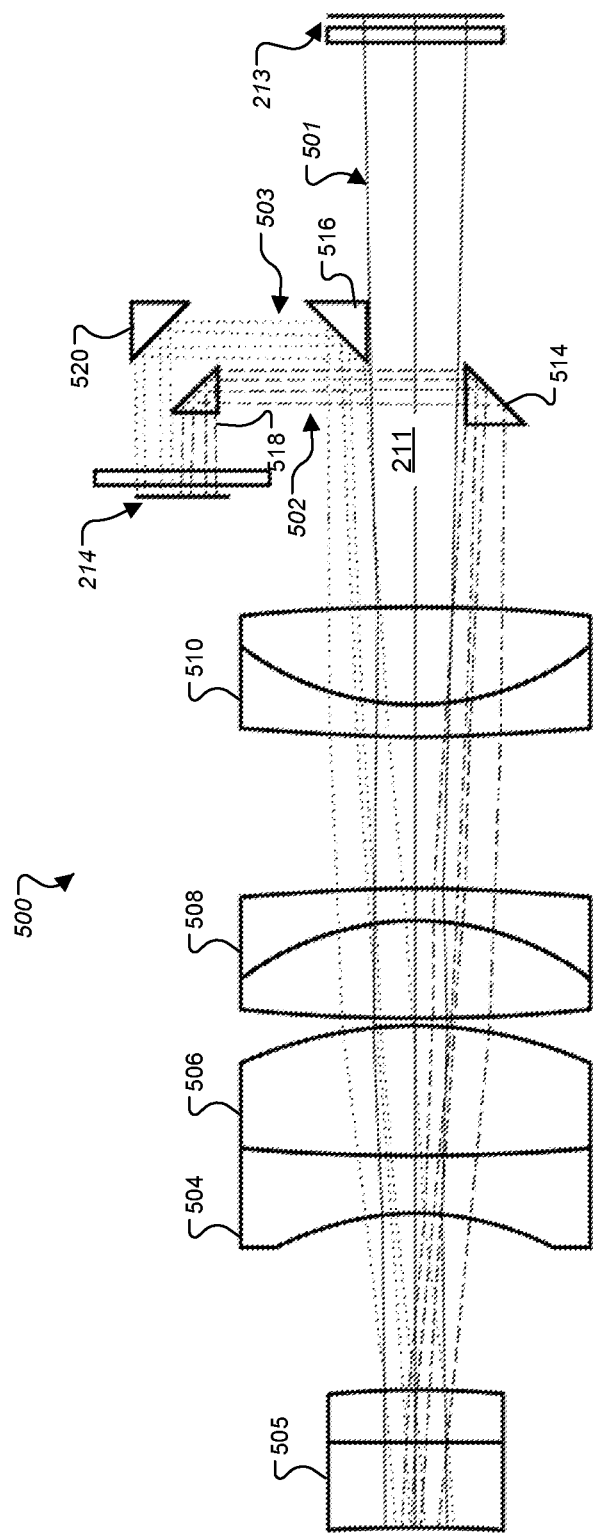
FIG. 5 is a ray bundle diagram of an optical instrument system according to an example embodiment of the present invention.
Figure 6:
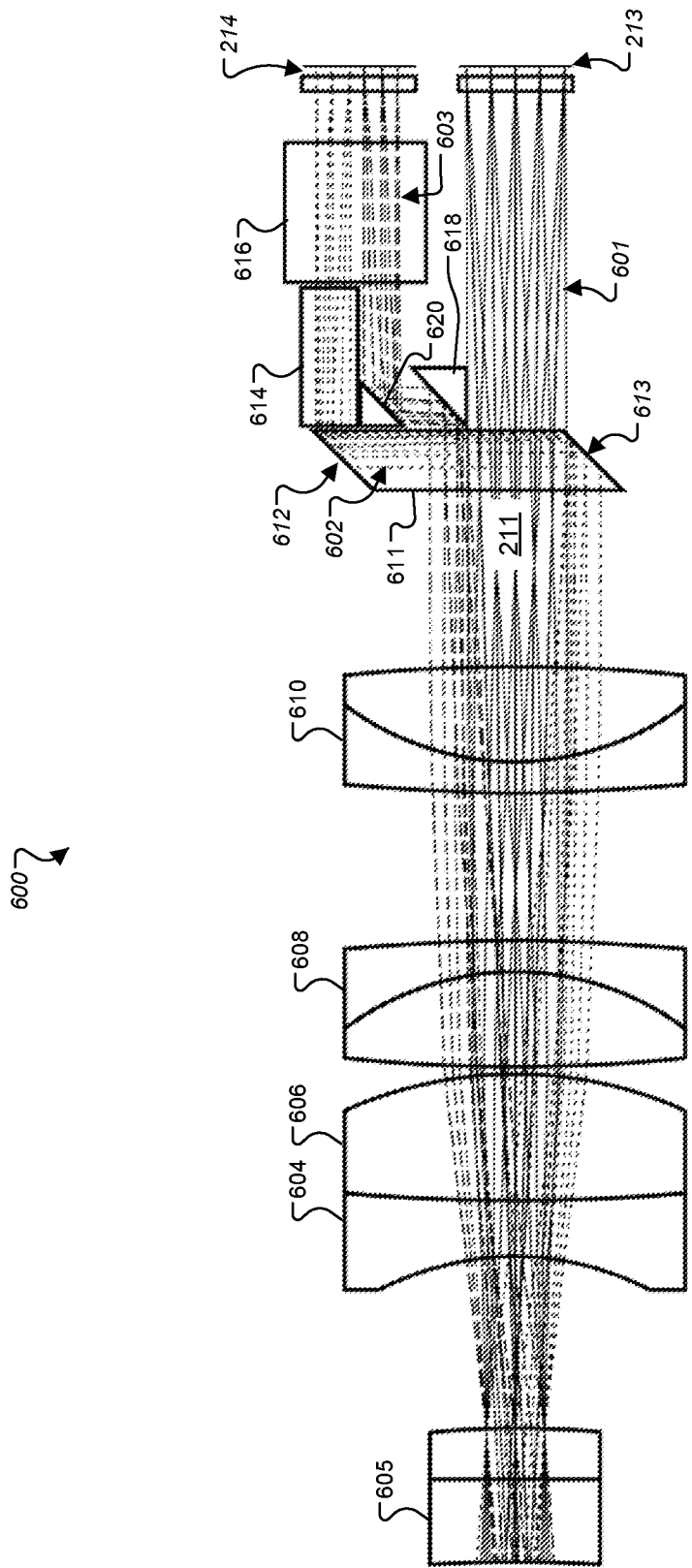
FIG. 6 is an illustration of an alternative optical system for an embodiment of the invention.
Figure 7:
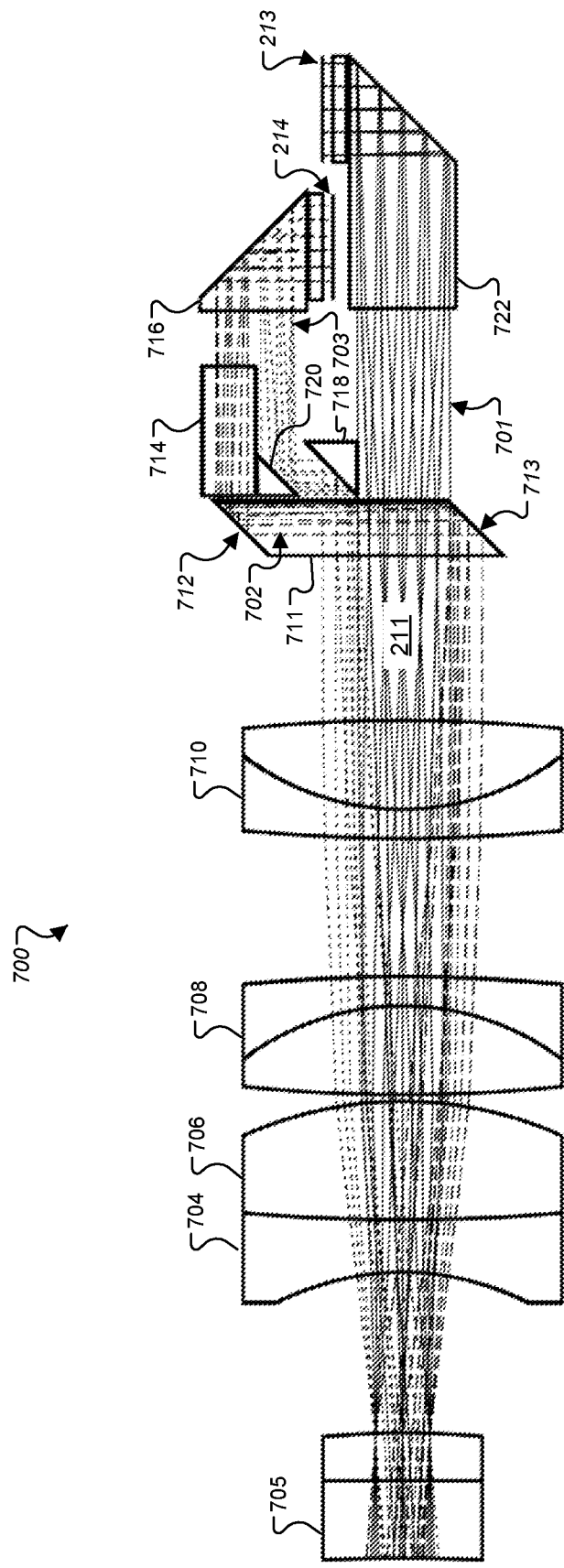
FIG. 7 is an illustration of another alternative arrangement of optical components in an embodiment of the invention.

FIG. 5, FIG. 6, and FIG. 7 represent alternative configurations that, like the embodiment of FIG. 4, minimize the rolling shutter effect as discussed above.

FIG. 5 is a light ray bundle diagram of a scope optical channel assembly 500 having a different construction of light directing elements according to another embodiment. The effect of optical assembly 500 can be seen in the depicted light ray bundles 501, 502, and 503 which show image light directed along the optical axis of optical assembly 500 and directed toward first image sensor 213 and second image sensor 214.

At the left is shown element 505, an element of optical channel assembly 500, in this case a conditioning lens receiving light from the scope element into the camera head. Optically arranged or attached at the proximal side of lens 505 is a lens 504, preferably a concave-concave lens with a negative power to spread the incoming light to an appropriate size for the imaging process downstream in the proximal direction. A convex-convex lens 506 is bonded to lens 504 in the downstream direction with a positive power. Next the light passes through an achromatic doublet 508 including a convex-convex lens and a meniscus lens. A similar achromatic doublet lens 510 is arranged with the meniscus lens facing lens 508 to receive the light from lens 508 and complete the optical manipulation to align the light for image space 211.

At the image space 211, the light emerges from the single channel optical system to focus on image sensors 213 and 214. In this embodiment, a first portion of image light 501 passes straight toward first image sensor 213. A second portion of the image light 502 is directed to second image sensor 214 by a reflective element 514 directing light 502 upward, and another reflective element 518 reflecting light 502 toward image sensor 214. A third portion of the image light 503 at the opposite side of first portion 501 from second portion 502 is also reflected toward second image sensor 214 by reflecting elements 516 and 520. Reflecting elements 514, 516, 518, and 520 may be mirrors or reflecting prisms.

The depicted arrangement receives the first portion of the image light 501 from the optical channel assembly with the first image sensor 213, forming a first image of a first part of the field of view of the (single) optical channel assembly, and receives second and third portions of the image light 502 and 503 from the optical channel assembly with the second image sensor 214, forming second and third images of respective portions of the field of view.

As can be understood, the different portions of light make up different areas from the common image light fed to image space 211 and provide different areas of the image viewable through the scope. The image light may be maintained in the same focal conditions along the depicted paths from reflecting elements 514 to 518, and reflecting elements 516 to 520 so that the two partial images can be easily reconstructed. The use of two reflecting elements in the light path for light 502 and light 503 allows simultaneous line-by-line scanning along both image sensors with reduced line artifacts in the combined image.

FIG. 6 shows a light ray bundle diagram of a scope optical channel assembly 600 having a different construction of light directing elements according to another embodiment. In this particular embodiment both sensors are positioned on the same plane, which is particularly beneficial as it enables the two sensors to potentially share a single circuit board, or, potentially, be elements of a single, larger sensor. The effect of optical assembly 600 can be seen in the depicted light ray bundles comprising portions of image light 601, 602, and 603 which show image light directed along the optical axis of optical assembly 600 and directed toward first image sensor 213 and second image sensor 214.

Elements 604, 605, 606, 608, and 610 are similar to elements 504-510 as described with respect to FIG. 5. At the image space 211, the light emerges from the single channel optical system to focus on image sensors 213 and 214. In this embodiment, a first portion of image light 601 passes straight toward first image sensor 213. A second portion of the image light 602 is directed to second image sensor 214 by a reflective interior surface 613 of irregular prism element 611, directing light 602 upward, and another reflective interior surface 612 reflecting image light 602 toward second image sensor 214. Second portion of image light 602 passes through optical block 614, and then optical block 616 to second image sensor 214 to maintain identical focal conditions to third portion of image light 603.

A third portion of the image light 603 at the opposite side of first portion of image light 601 from second portion of image light 602 passes straight through irregular prism element 611 and is then reflected toward second image sensor 214 by reflecting elements 618 and 620. Reflecting elements 618, and 620 may be mirrors or reflecting prisms. Third portion of image light 603 passes through optical block 616 before hitting second image sensor 214 to maintain identical focal conditions to second portion of image light 602.

The depicted arrangement receives the first portion of the image light 601 from the optical channel assembly with the first image sensor 213, forming a first image of a first part of the field of view of the (single) optical channel assembly, and receives second and third portions of the image light 602 and 603 from the optical channel assembly with the second image sensor 214, forming second and third images of respective portions of the field of view.

As can be understood, the different portions of light make up different areas from the common image light fed to image space 211 and provide different areas of the image viewable through the scope. The image light may be maintained in the same focal conditions along the depicted paths, each including two reflections, so that the two partial images can be easily reconstructed. The use of two reflecting elements in the light path for light 602 and light 603 allows simultaneous line-by-line scanning along both image sensors with reduced line artifacts in the combined image.

FIG. 7 depicts an embodiment of the present invention which may be particularly advantageous in distal tip implementations of the invention. A light ray bundle diagram of a scope optical channel assembly 700 having a different construction of light directing elements is shown. The effect of optical assembly 700 can be seen in the depicted light ray bundles comprising portions of image light 701, 702, and 703 which show image light directed along the optical axis of optical assembly 700 and directed toward first image sensor 213 and second image sensor 214. For distal tip implementations, for which this embodiment is particularly well suited, some optical elements for conditioning incoming light from a scope (705) may be omitted, or replaced by objective optical elements as are known in the art.

Elements 704, 705, 706, 708, and 710 are similar to elements 504-510 as described with respect to FIG. 5. At the image space 211, the light emerges from the single channel optical system to be directed at image sensors 213 and 214. In this embodiment, a first portion of image light 701 passes straight through irregular prism element 711 and into reflective prism 722. First portion of image light 701 is then reflected upward off an interior reflective surface of reflective prism 722 toward first image sensor 213.

A second portion of the image light 702 is directed to second image sensor 214 by a reflective interior surface 713 of irregular prism element 711, directing light 702 upward, and another reflective interior surface 712 reflecting light 702 toward second image sensor 214. Second portion of image light 702 passes through optical block 714, and then into reflective prism 716, where it is reflected downward to second image sensor 214.

A third portion of the image light 703 at the opposite side of first portion 701 from second portion 702 passes straight through irregular prism element 711 and is then reflected toward second image sensor 214 by reflecting elements 718 and 720. Reflecting elements 718, and 720 may be mirrors or reflecting prisms. Third portion of image light 703 passes into reflecting prism 716 and is reflected downward to hit second image sensor 214.

The depicted arrangement receives the first portion of the image light 701 from the optical channel assembly with the first image sensor 213, forming a first image of a first part of the field of view of the (single) optical channel assembly, and receives second and third portions of the image light 702 and 703 from the optical channel assembly with the second image sensor 214, forming second and third images of respective portions of the field of view.

As can be understood, the different portions of light make up different areas from the common image light fed to image space 211 and provide different areas of the image viewable through the scope. The image light may be maintained in the same focal conditions along the depicted paths, each including two reflections, so that the two partial images can be easily reconstructed. In this embodiment the first portion of image light 701 is reflected one time, while the second and third portions of light 702 and 703 are reflected three times, providing the same mirror orientation as first portion of image light 701. This arrangement allows simultaneous line-by-line scanning along both image sensors with reduced line artifacts in the combined image. As mentioned above, this embodiment is particularly beneficial in distal tip implementations of the invention, as both sensors are positioned in the same, or nearly the same, plane perpendicular to the shaft distal end 105, and in this way the circuit board (or boards) containing the sensors can be positioned along the shaft at its maximum inner diameter, maximizing, thereby, the possible size of the sensors and/or minimizing the diameter of the shaft for a given sensor size.

Figure 8:
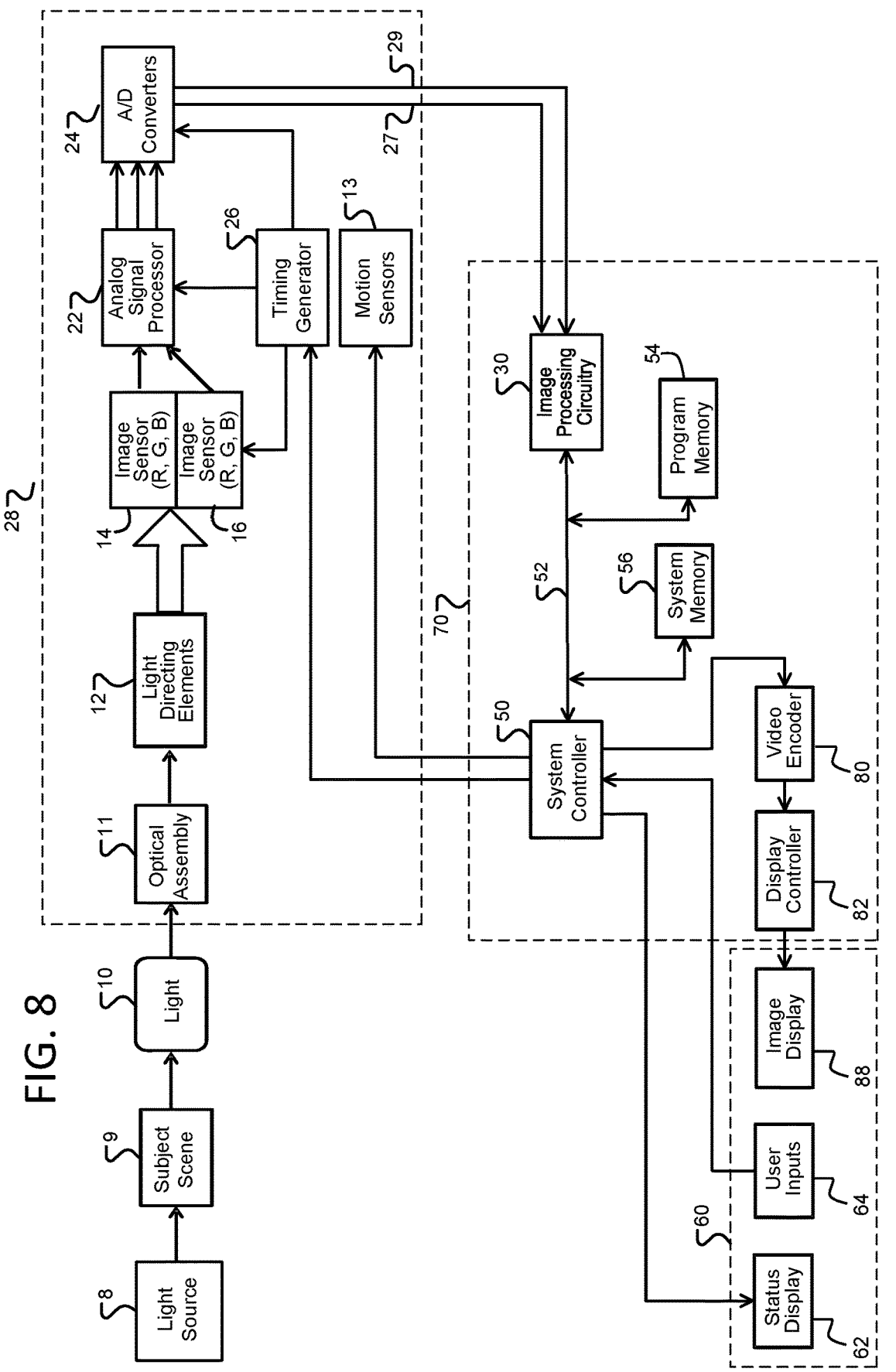
FIG. 8 is a block diagram of the optical instrument and image processing system.

FIG. 8 is a block diagram of an optical instrument system according to an example embodiment of the present invention. While this example circuit is shown for an endoscope, the present invention is applicable to more than one type of medical scope instrument, but typically is applicable for scope applications that employ image capture at the instrument distal tip, such as endoscopes, borescopes, or exoscopes, for example.

A light source 8 illuminates subject scene 9 and light 10 reflected from (or, alternatively, as in the case of certain fluorescent or digital microscope arrangements, transmitted or emitted by) the subject scene forms an optical image via an optical channel assembly 11, where the light is focused, typically aligned with the scope axis or a desired optical axis, and passed to a proximal side of optical channel assembly 11 where light directing elements 12 direct different portions of the light to form different portions of the image on two solid-state image sensors 14 and 16.

In the present invention, optical channel assembly 11 includes a single-channel imaging system and may be constructed according to a large variety of known methods suitable for placement in a scope distal tip or camera head, including the preferred optical channel assembly of FIG. 3. Image sensors 14 and 16 convert the incident light to an electrical signal by, for example, integrating charge for each picture element (pixel). The image sensors 14 and 16 may be active-pixel type complementary metal oxide semiconductor sensors (CMOS APS) or a charge-coupled devices (CCD), to give just two possible examples. The output analog signal from the image sensors is processed by analog signal processor 22 and applied to analog-to-digital (A/D) converter 24 for digitizing the analog sensor signals. In some versions (typically CMOS designs), the analog signal processing and A/D converters may be integrated into individual sensor models attached to each sensor 14 and 16.

The system's camera 28 generally includes timing generator 26, which produces various clocking signals to select rows and pixels and synchronizes the operation of image sensors 14 and 16, analog signal processor 22, and A/D converter 24. One or more motion sensors 13 such as, for example, an accelerometer, gyro, or magnetometer, may be mounted in the endoscope shaft, tip, or handle to aid in detecting movement, including rotation, of the endoscope. A scope distal tip electronic assembly typically houses image sensors 14 and 16, while the locations of each of analog signal processor 22, the A/D converter 24, and the timing generator 26 may vary, for example in the scope handle 102 or partially integrated into the distal tip electronic assembly. The functional elements of the camera 28 may be fabricated as a single integrated circuit as is commonly done with CMOS image sensors or they may be separately fabricated integrated circuits.

The system controller 50 controls the overall operation of the image capture device based on a software program stored in program memory 54. This memory can also be used to store user setting selections and other data to be preserved when the camera 28 is turned off. Data connections 27 and 29 carry the digital image data of image sensors 14 and 16, respectively, to image processing circuitry 30, which may be integrated with system controller 50 in some versions or may be a separate programmable logic device or data processor. A data bus 52 provides a pathway for address, data, and control signals. In some variations, data bus 52 may also carry data connections 27 and 29.

Image processing circuitry 30 performs image processing operations including the operations to combine the three partial images from image sensors 14 and 16, as necessary, and to perform rotation functions as further described below. Image processing circuitry 30 is operable to combine image data from the first and second image data into a displayed image including image data from the first and second portions of the second image sensor 16 positioned at opposite sides of the displayed image with the first image data from first image sensor 14 displayed there between. Processed image data are continuously sent to video encoder 80 to produce a video signal. This signal is processed by display controller 82 and presented on image display 88. This display is typically an HD, UHD, or 4K format liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 may manage the graphical user interface (GUI) presented on one or more of the displays (e.g. on image display 88). The GUI typically includes menus for making various option selections.

Image processing circuitry 30, system controller 50, system and program memories 56 and 54, video encoder 80, and display controller 82 may be housed within camera control unit (CCU) 70. CCU 70 may be responsible for powering and controlling light source 8 and/or camera 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

Figure 9:
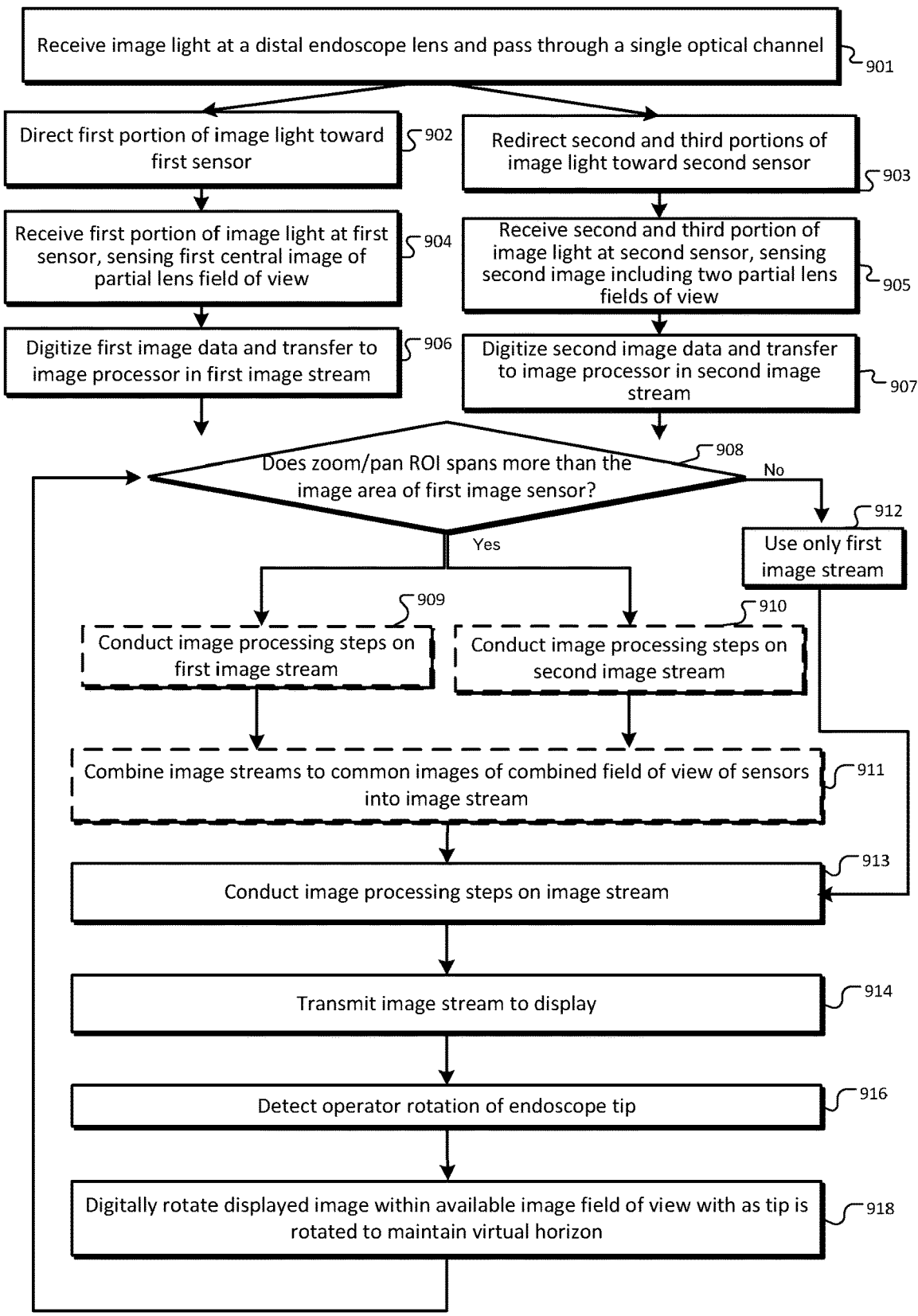
FIG. 9 is a flowchart of an example process for combining and rotating the partial images received from the multiple sensors according to some embodiments.

FIG. 9 is a flowchart of an example process for combining and rotating the partial images received from the multiple sensors according to some embodiments, which may be employed with the example hardware and camera designs herein, or may be employed with other hardware designated with a similar purpose, such as software program code executed by a GPU or other image processor. The depicted process starts at block 901 with receiving image light at a distal lens of an optical assembly and passing the image light through a single optical channel.

Next at block 902, the process directs a first portion of the image light toward the first sensor. Second and third portions of the image light is also be directed at a non-zero angle to the longitudinal axis of the endoscope at block 903. As can be understood blocks 902 and 903 may be performed by two different light directing elements or a single light directing element such as a compound prism.

At block 904 the process receives the first portion of the image light from the optical channel assembly with the first image sensor, the first portion of the image light forming a first image of a first part of the field of view of the distal lens. This image stream is digitized and transferred to an image processor at block 906. Simultaneously at block 905 the process receives the second and third portions of the image light from the optical assembly with the second image sensor to produce second and third image streams at block 907, both provided through the second image sensor in this embodiment. The second and third portions of the image light are from opposing sides of the image light with respect to the first portion and at least substantially different from the first portion. By substantially different it is meant that the majority of image is different, while relatively small portions may overlap with the first portion of image light. That is, the first image preferably has a partially overlapping field of view with the second and third images, assisting in registration of the collected images.

At block 908, the process determines if the region of interest (ROI), that is the image area to be displayed, as selected by a digital zoom indication received from a user, a digital pan indication received by a user, and a rotation indication received by the instrument, spans more than the image area received by the first image detector. Typically block 908 will be skipped the first iteration through the process, until zoom and rotation inputs are received. (In some embodiments there will be no digital zoom implementation, and therefore, this step will not be relevant.) If so, the process goes to blocks 909 and 910, where image processing steps are conducted on both image streams. At block 911, the process includes combining the first, second and third images to produce an image of the combined field of view of the sensors, when the ROI spans more than the image area of the first image sensor. If the ROI does not span more than the first image sensor at block 908, the process goes to block 912 where it selects only the first image stream for processing thus saving processing cycles and increasing power efficiency of the overall process. The combined image typically has a higher resolution than would otherwise be possible with a single sensor. Block 911 may include steps to adjust for relative misalignment of the sensors, such as applying a rotation to image data from one or both sensors (preferably provided in calibration of the instrument), and may include recognizing edges at the edges of the first, second, and third images so that those edges can by aligned in the combined image.

The depicted process blocks that are in parallel are typically performed with parallel processing, as are many of the other processing functions in preferred designs. At blocks 909 and 910, the process may perform one or more image processing steps, with these shown in dotted lines to indicate it is optional in some embodiments.

If overlapping pixels are available as described above, the process may include cross-correlating these overlapping pixels to find the highest point of alignment, or applying a shift to one or both of the images to account for an offset detected in calibration. Such edge detection and correlation are known in the art and will not be further described. The combined image is then subjected (at block 913) to image processing such as dynamic range adjustment, filtering, color range adjustment, feature recognition, and any other suitable image processing techniques for endoscopic imaging.

Figure 10:
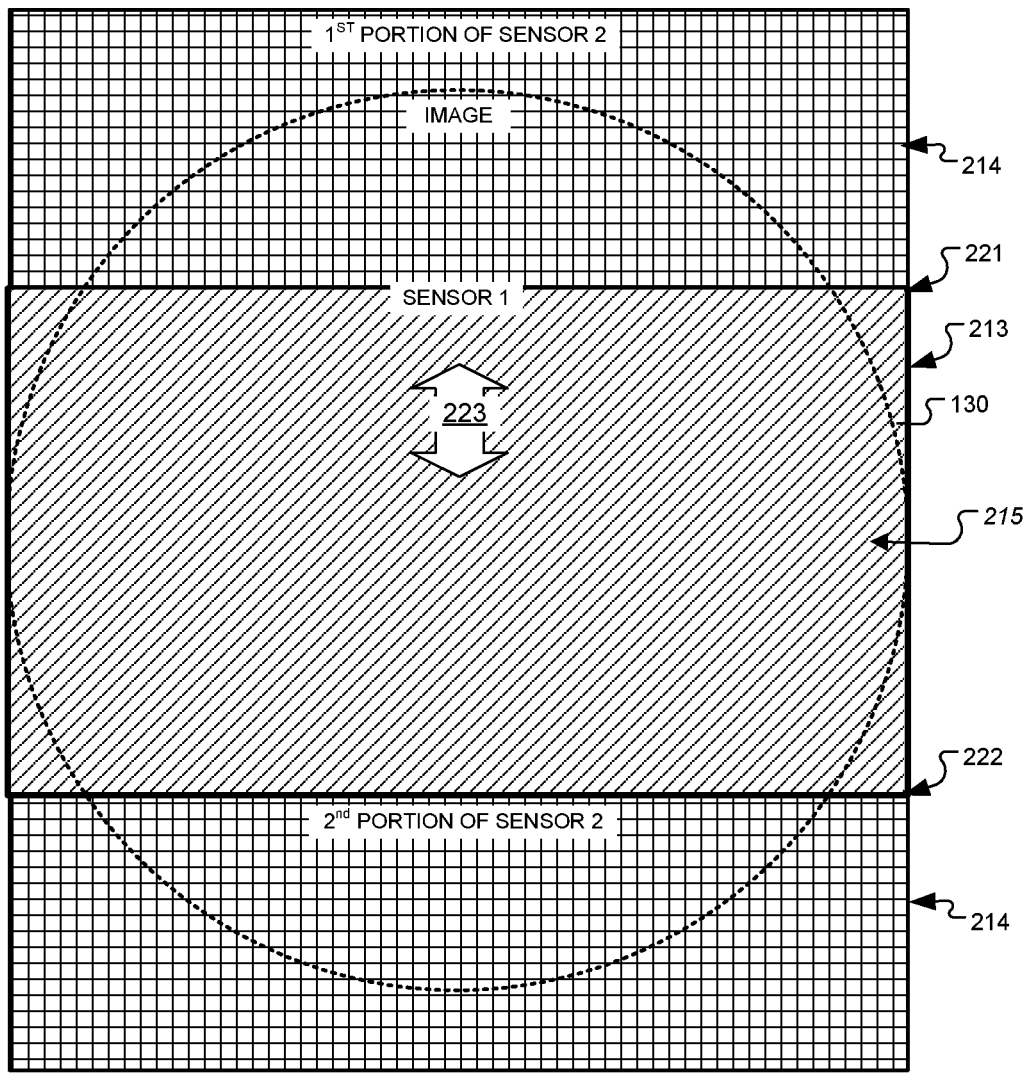
FIG. 10 is a diagram showing a displayed area selected from within the combined image sensor field of view according to an example embodiment.

The combined image or a selected sub-image from the total combined image are transmitted to an electronic display for display to the operator at block 914 and may also be recorded and saved with any suitable video or image recording format. The entire image is then available for viewing, image processing, and manipulation according to any suitable medical imagery techniques. In some scenarios, the entire combined image may be displayed, while in others a desired aspect ratio (for example that of a standard HD display) image smaller than the total image may be selected out of the entire combined image for display, allowing panning of the displayed image within the overall collected image area. A diagram of such an image may be seen in FIG. 10, in which the combined field of view of a first sensor 213 and a second sensor 214 are shown each with a different fill pattern. The circle 130 represents the area of the image light coming from the round lens that is captured by the combination of the two sensors 213 and 214. As can be understood from the diagram of FIG. 10, the second sensor 214 receives image light from opposing sides of the central image light hitting the first sensor 213. These portions of image light are received by the depicted first and second portions of second sensor 214, forming a second and third images of second and third parts of the field of view of the distal lens at least substantially different from the first part of the field of view received at first sensor 213. As is made clear from FIG. 10, seams 221, 222 between the collected images are present in the overall presented image if the zoom, pan, and rotation settings require a combined image stream. At these seams, the images collected by the two image sensors 213, 214 are reassembled by image processing circuitry. While high quality image processing seeks to minimize any apparent visual artifacts created by combining these disparate regions of the two sensors, some artifacts are likely to be present at and around these seams. However, it is a primary benefit offered by the present invention that the central region of the image, which generally contains the primary region of interest (ROI), that is the area of the overall viewed object space of most interest to the operator, contains no seam and therefore is not subject to any image processing artifacts associated with reassembly of the image. Further, as is shown clearly in FIG. 10, when the displayed image 215 falls completely within the area captured by the first image sensor 213, there is no need to apply any image processing to reassemble the image, saving valuable computer processing power. Of course, if the entire image is to be recorded, such processing may still be performed, or alternatively, the images received by each detector may be recorded individually and reassembly processing may be performed as necessary at a later time. The displayed image area 215 may be digitally panned, as indicated in the example scenario shown in FIG. 10 by the arrow 223, and once the displayed image area encompasses data collected by the second image sensor, appropriate image processing may be engaged to provide a combined image as necessary to fill the displayed image area.

Referring again to FIG. 9, while displaying the combined image stream, at block 916 the process detects the physical rotation of the scope distal end, which may be through sensors such as motion sensors 13 and recognized by the system controller 50. In some embodiments, detecting rotation may also be done by detecting such rotation in the received stream of images through image processing. An operator may set the current orientation as the desired viewing orientation through the user interface 64 or through a button on the scope handle, for example, after which the process will digitally rotate the display to make counter-rotations to the displayed images in the opposite direction of the scope physical location to maintain 'virtual horizon' constant viewing orientation as shown at block 918.

Figure 11A:
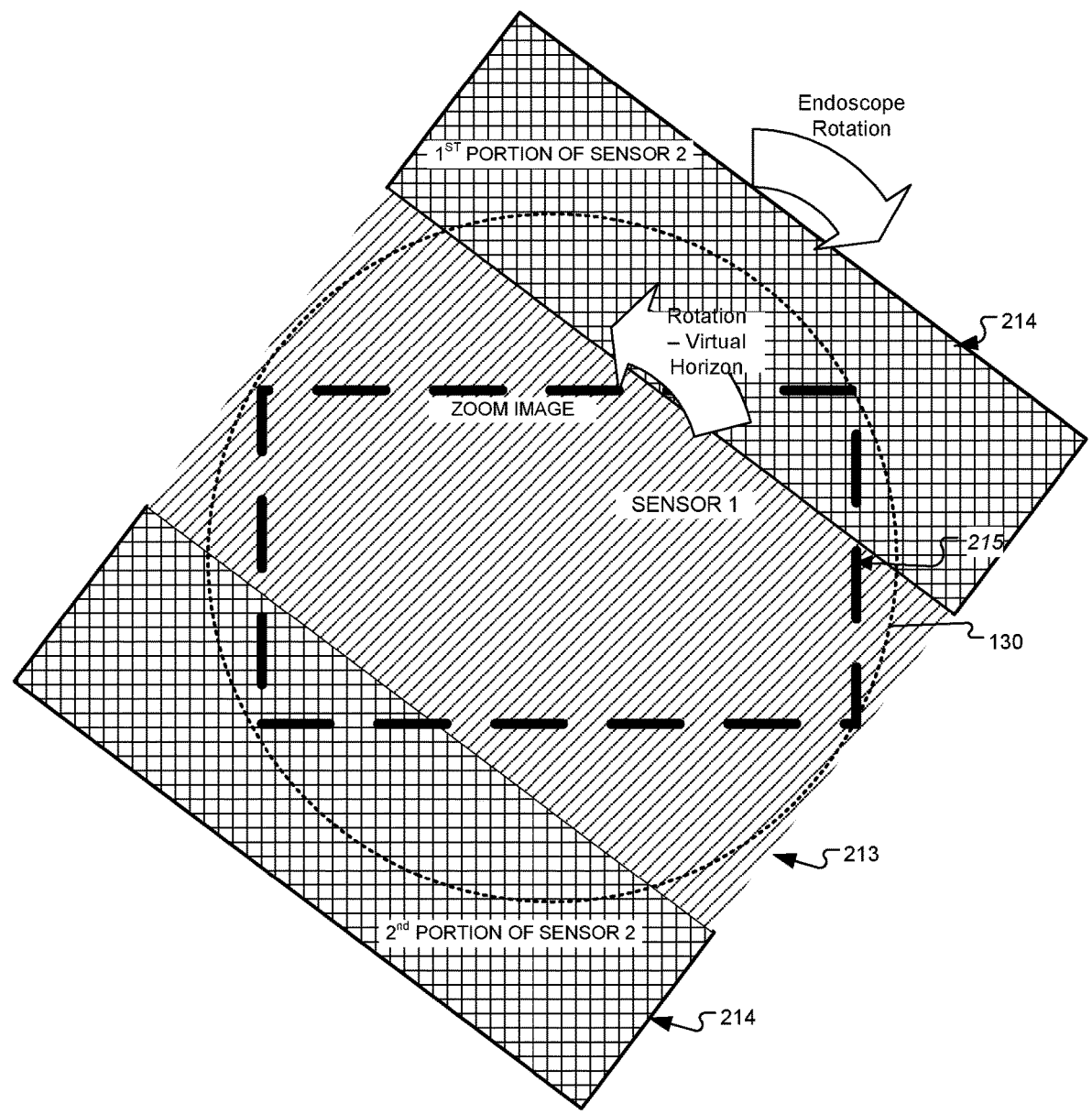
FIG. 11A is a diagram showing digital rotation of a displayed area within the combined image sensor field of view to provide a virtual horizon.

The orientation of the displayed image is kept constant, as shown in the diagram of FIG. 11A, by the process of selecting the view over different portions of the partial images received from the image sensors, in which the combined field of view of a first sensor 213 and a second sensor 214 are shown each with a different fill pattern. As depicted in this example diagram, an operator rotating the endoscope in the clock-wise direction causes the process to counter-rotate the image in the counter-clockwise direction within the available field of view, maintaining the view orientation to avoid the common problem of operator visual disorientation during examination procedures. The opposite physical rotation of course causes an opposite digital rotation. While this version provides a displayed image area that is able to maintain the depicted aspect ratio (16:9) while displaying a full image 215 using data from both sensors, other operating modes may be provided to display a larger portion of the total imaged area, or all of the image area. In this case, as long as the diagonal of the displayed image area 215 is equal to or smaller than the collected lens field of view 130, the image can be rotated, without displaying any non-image information (generally data containing only dark pixels, as no light is detected in these regions outside of the field of view). As the image is rotated, and the displayed region 215 contains data collected from both image sensors 213,214, image processing may be engaged to recombine the images as necessary, as well as performing virtual-horizon maintaining processing.

Figure 11B:
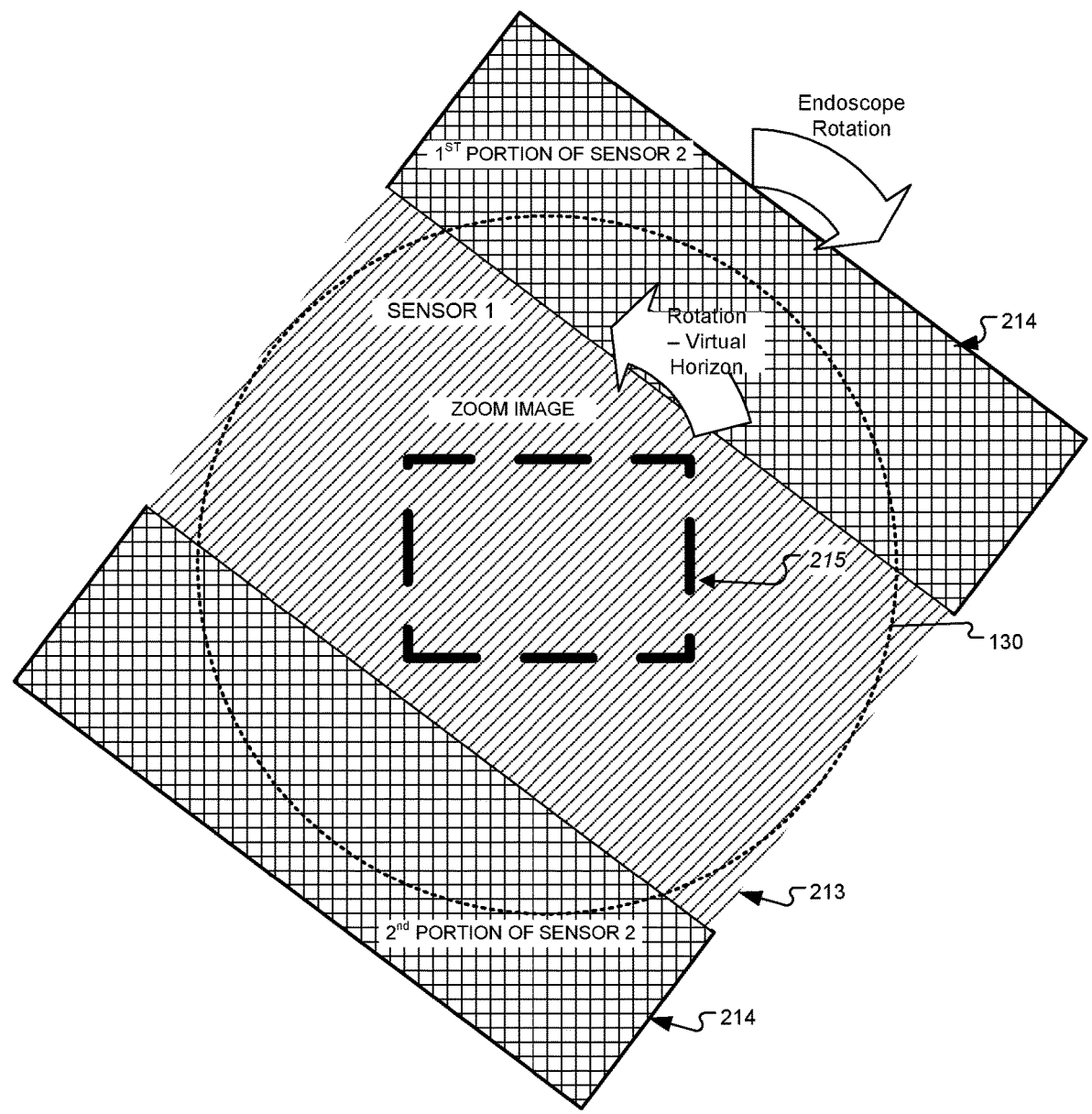
FIG. 11B is a diagram showing digital rotation of a digitally zoomed display area within the combined image sensor field of view.

FIG. 11B shows in diagram form an example of rotating a digitally zoomed image within the field of view shown in FIG. 11A. The illustrated process receives a digital zoom signal indicator indicating a portion of the available image area as a desired image area to be displayed as image 215. Digital zooming, as is known in the art, generally comprises the step of selecting a portion of the available image data and displaying only this portion and conforming the zoomed region 215 to fill the display as completely as possible. In this example scenario, the portion identified is wholly contained within the image area of the first sensor 213. In the process, if the desired image area 215 spans only image data contained in the first image from first image sensor 213, the process produces a displayed image from the image data collected from only the first sensor, therefore image processing is not required to combine image data from the second image sensor 214. Further, if a diagonal of the displayed image 215, generally the ROI, is smaller than the height of the central region produced by first image sensor 213, and the ROI 215 is appropriately located, as is the case in FIG. 11B, the endoscope may be rotated and a virtual horizon maintained, without the need to perform additional image processing required to combine the image data received from the second image sensor 214 with that of the first image sensor 213. As discussed above, however, the image data from both sensors can be collected and stored for later combination as necessary. If the desired image area spans image data from the first and the second or third images, via digital panning (further discussed below), digital zooming, endoscope rotation, or a combination thereof, the image processor combines data from the first and one or both of the second and third images to produce a displayed image. For example, if the depicted desired image 215 were panned to the right, it would overlap with the 1$^{st}$ portion of second sensor 214, causing image data from that portion to be combined with image data from first image sensor 213 to produce a displayed image.

Figure 12:
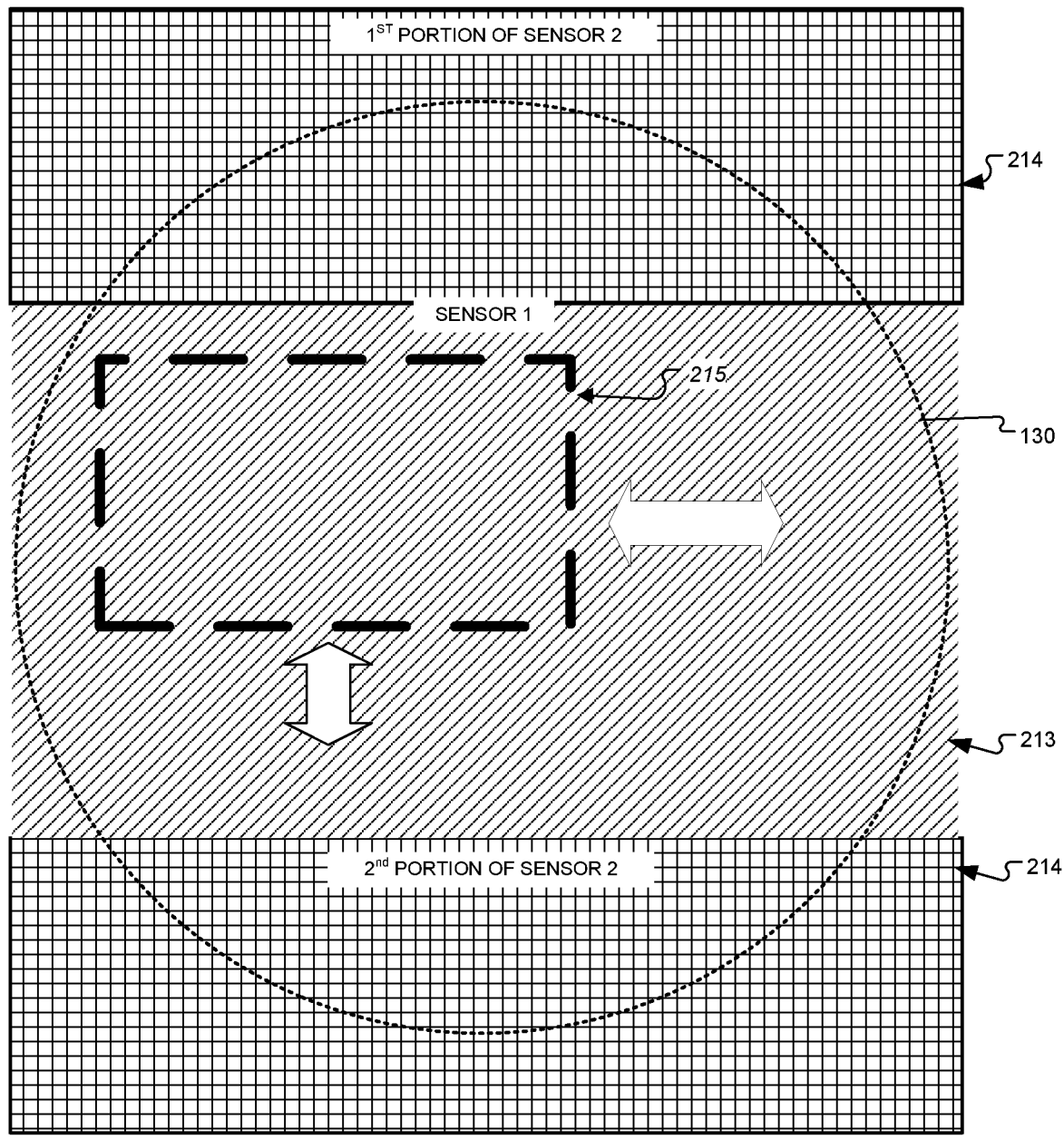
FIG. 12 is an example diagram of a digital panning function within the combined image sensor field of view.

FIG. 12 shows an example diagram of another ROI display area 215 showing digital panning over the available combined image area. As can be seen from the overlay of the lens field of view 130 on the diagram, this version does not make full use of the lens field of view. The image processing system can determine if the ROI 215 is contained wholly within the boundaries of the central sensor and adjust processing procedures accordingly. It can also permit digital panning, that is the movement of the displayed, digitally zoomed ROI within the available area of the first sensor without additional processing necessary to combine data from the image sensors. Digital panning along the combined image may also be provided in any of the embodiments, in which the up/down and right/left arrows shown in FIG. 12 shows how a display area may be panned along the available combined image data. The vertical direction of the diagram represents the vertical direction of the wide angle lens field of view in the diagram of FIG. 2. In some versions or modes, rotation of the view may cause "vignetting" or rounded off dark corners or edges where the desired display area exceeds the available image data from the combined image from the sensors. In some implementations a processing unit may correct or modify the distortion characteristics of the image.

Because digital cameras employing endoscopic instruments and related circuitry for signal capture, processing, and correction and for exposure control are well-known, the above description is directed in particular to elements forming part of, or cooperating more directly with, a method and apparatus in accordance with the present invention. Elements not specifically shown or described herein are selected from those known in the art. Certain aspects of the embodiments may be provided in software. Given the system as shown and described according to the invention in the following materials, software not specifically shown, described or suggested herein that is useful for implementation of the invention is conventional and within the ordinary skill in such arts.

The invention being thus described, it will be obvious that the same may be varied in many ways. Such variations are not to be regarded as a departure from the scope of the invention, and all such modifications as would be obvious to one skilled in the art are intended to be included within the scope of the following claims. For example, reference to an endoscope is intended merely as a representative example application and is not intended to be limiting. Implementations include optical scopes such as exoscopes and borescopes. Further, although sensors 213 and 214 are shown as discreet entities, two or more of said sensors may share, for example, a mounting substrate or housing accommodating said two or more sensors.

Further still, although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

What is claimed is:

1. An optical instrument system comprising an endoscopic instrument, the endoscopic instrument including:
    (a) an optical channel assembly including a single channel lens system optically arranged to receive image light from an object space and condition the image light in a single optical channel to create an image space;
    (b) first and second image sensors, the first image sensor positioned to receive a first portion, but not all, of the image light, the first portion of image light corresponding to a first central area of an optical image, and the second sensor positioned to receive a second portion and a third portion of the image light from opposing sides of the image with respect to the first portion and at least substantially different from the first portion of image light; and
    (c) first and second light directing elements positioned in the image space of the optical channel assembly to receive the second and third portions of the image light from the optical channel assembly and direct them toward respective first and second portions of the second image sensor.

2. The optical instrument system of claim 1, wherein the optical channel assembly extends from a distal end portion of an instrument shaft coupled to a proximal camera head holding the first and second image sensors.

3. The optical instrument system of claim 1, wherein the optical channel assembly is housed in a distal end portion of an instrument shaft with the first and second image sensors.

4. The optical instrument system of claim 1 wherein the first portion of image light partially overlaps with at least one of the second and third portions of image light.

5. The optical instrument system of claim 1 further comprising image processing circuitry operatively coupled to the first and second image sensors to receive first and second image data from the sensors and operable to combine image data from the first and second image data into a displayed image including image data from the first and second portions of the second image sensor positioned at opposite sides of the displayed image with the first image data displayed there between.

6. The optical instrument system of claim 5, in which the image processing circuitry is further operable to receive a zoom input control, and in response alter the displayed image to display an enlarged portion of the displayed image including only image data received from the first image sensor.

7. The optical instrument system of claim 6, wherein the image processing circuitry is further operable to, when a user rotates the endoscopic instrument around an instrument shaft, rotate the displayed image to provide a view with a constant horizon.

8. The optical instrument system of claim 6, wherein the image processing circuitry is further operable to detect when a zoomed image is produced entirely within an area of the image data received from the first image sensor, and further operable to disable image processing necessary to combine the first and second image data.

9. The optical instrument of claim 6, wherein the image processing circuitry is further operable to: detect, when a user rotates the endoscopic instrument around an instrument shaft, if a zoomed image is produced with a diagonal of the zoomed image entirely within an area of image data received from the first image sensor, and electronically rotate the displayed image to provide a view with a constant horizon, and disable image processing necessary to combine the first and second image data.

10. The optical instrument system of claim 1, in which the second and third portions of image light are directed toward the second image sensor along an optical axis that is non-parallel to a longitudinal axis of the optical channel assembly.

11. The optical instrument system of claim 10, in which the plane of the second image sensor is at an angle offset enough from parallel to the longitudinal axis of the optical channel assembly such that reflections are mitigated.

12. The optical instrument system of claim 1, in which the first light directing element comprises a prism which passes the first portion of image light to the first sensor and redirects the second portion of the image light to the second sensor.

13. The optical instrument system of claim 12, in which the second light directing element comprises a mirror.

14. The optical instrument system of claim 12, in which the second light directing element comprises a reflective prism.

15. The optical instrument system of claim 1, further comprising a third light directing element redirecting the first portion of image light toward the first sensor.

16. The optical instrument of claim 15, wherein the third light directing element also comprises reflective surfaces positioned to direct the second and third portions of image light.

17. The optical instrument of claim 1, wherein the second portion of image light and the third portion of image light are each reflected with at least two reflective elements providing, thereby, a mirror image orientation of the second and third portions of image light captured at the second sensor that is the same as an orientation of as an image the first portion of image light captured on the first sensor.

18. A method of providing images through an endoscope, the method comprising:

receiving image light at a distal lens of an optical channel assembly and passing the image light through a single optical channel path toward an image space;

receiving a first portion of the image light from the optical channel assembly with a first image sensor, the first portion of the image light forming a first image of a first part of a field of view of the distal lens;

receiving second and third portions of the image light from the optical channel assembly with a 2 second image sensor, the second and third portions of the image light from opposing sides of the image light with respect to the first portion and forming second and third images of second and third parts of the field of view of the distal lens at least substantially different from the first part of the field of view; and combining, with an image processor, the first, second, and third images to produce a displayed image.

19. The method of claim 18, further comprising, responsive to a user rotating the endoscope around a shaft, rotating the displayed image to provide a view with a constant horizon.

20. The method of claim 18, further comprising receiving a zoom input control and in response altering the displayed image to display an enlarged portion of the displayed image including a center of the displayed image, the enlarged portion consisting entirely of image data received from the first image sensor.

21. The method of claim 18 in which the second and third portions of the image light are directed toward the second image sensor along an optical axis that is non-parallel to a longitudinal axis of the optical channel assembly.

22. The method of claim 18 in which in which a plane of the second image sensor is at an angle slightly offset from parallel to longitudinal axis of the optical channel assembly.

23. The method of claim 18, further comprising splitting the second portion of image light toward the second sensor and passing the first portion of light to the first sensor with a prism.

24. The method of claim 23, further comprising redirecting the third portion of the image light with one of a mirror or a reflective prism.

25. The method of claim 18, further comprising redirecting the first portion of image light toward the first image sensor with a reflective element.

26. The method of claim 18, further comprising directing the second portion of image light and the third portion of image light to at least two reflective elements to provide, thereby, a mirror image orientation of the second and third portion of image light captured at the second sensor that is the same as an orientation of an image of the first portion of image light captured on the first sensor.

27. A method of providing images through an endoscope, the method comprising:

receiving image light at a distal lens of an optical assembly and passing the image light through a single optical channel path toward an image space;

receiving a first portion of the image light from the optical channel assembly with a first image sensor, with a first sensor height smaller than a first sensor width, the first portion of the image light forming a first image of a first part of a field of view of the distal lens;

receiving second and third portions of the image light from the optical channel assembly with a second image sensor, the second and third portions of the image light from opposing sides of the image light with respect to the first portion and forming second and third images of second and third parts of the field of view of the distal lens at least substantially different from the first part of the field of view;

providing an available image data area as the image data collected by a first portion of the second sensor, the first sensor, and a second portion of the second sensor;

receiving a digital zoom signal indicator indicating a portion of the available image area as a desired image area to be displayed;

if the desired image area spans only image data contained in the first image, producing a displayed image from the image data collected from only the first sensor; and if the desired image area spans image data from the first and the second or third images, combining, with an image processor, data from the first image and one or both of the second and third images to produce a displayed image.

28. The method of claim 27, further comprising, responsive to a user rotating the endoscope around an instrument shaft, rotating the displayed image to provide a view with a constant horizon, the displayed view being comprised entirely of image data collected from the first sensor if the desired image area spans only image data contained in the first image, and a displayed view being comprised of combined data from the first and one or both of the second and third images if the desired image area spans image data from the first and the 18 second or third images.

* * * * *